US010954473B2

(12) United States Patent
Brunn et al.

(10) Patent No.: US 10,954,473 B2
(45) Date of Patent: Mar. 23, 2021

(54) AQUEOUS SURFACTANT COMPOSITIONS

(71) Applicant: BASF SE, Ludwigshafen am Rhein (DE)

(72) Inventors: Claudia Brunn, Düsseldorf-Holthausen (DE); Ansgar Behler, Düsseldorf-Holthausen (DE); Hans-Christian Raths, Düsseldorf-Holthausen (DE); Detlev Stanislowski, Düsseldorf-Holthausen (DE); Gerhard Hermanns, Solingen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/301,466

(22) PCT Filed: May 11, 2017

(86) PCT No.: PCT/EP2017/061266
§ 371 (c)(1),
(2) Date: Nov. 14, 2018

(87) PCT Pub. No.: WO2017/198527
PCT Pub. Date: Nov. 23, 2017

(65) Prior Publication Data
US 2019/0292492 A1 Sep. 26, 2019

(30) Foreign Application Priority Data
May 18, 2016 (EP) ..................... 16170189

(51) Int. Cl.
A61K 8/00 (2006.01)
C11D 1/94 (2006.01)
A61K 8/04 (2006.01)
A61K 8/23 (2006.01)
A61K 8/36 (2006.01)
(Continued)

(52) U.S. Cl.
CPC .............. C11D 1/94 (2013.01); A61K 8/046 (2013.01); A61K 8/23 (2013.01); A61K 8/361 (2013.01); A61K 8/442 (2013.01); A61K 8/466 (2013.01); A61K 8/602 (2013.01); A61Q 5/02 (2013.01); A61Q 9/02 (2013.01); A61Q 11/00 (2013.01); A61Q 19/10 (2013.01); C11D 1/37 (2013.01); C11D 3/0094 (2013.01); C11D 3/046 (2013.01); C11D 10/042 (2013.01); A61K 2800/596 (2013.01); C11D 1/04 (2013.01); C11D 1/12 (2013.01); C11D 1/28 (2013.01); C11D 1/662 (2013.01); C11D 1/90 (2013.01)

(58) Field of Classification Search
None
See application file for complete search history.

(56) References Cited

U.S. PATENT DOCUMENTS 2,195,088 A * 3/1940 Keppler ............... C07C 309/07
562/109
6,172,026 B1 * 1/2001 Ospinal .................. C11D 1/37
510/152
(Continued)

FOREIGN PATENT DOCUMENTS

DE 4220580 A1 1/1994
EP 2 902 010 A1 8/2015
(Continued)

OTHER PUBLICATIONS

International Search Report for Patent Application No. PCT/EP2017/061266, dated Jun. 20, 2017.

Primary Examiner — Necholus Ogden, Jr.
(74) Attorney, Agent, or Firm — Marshall, Gerstein & Borun LLP

(57) ABSTRACT

Aqueous surfactant compositions comprising
one or more alpha-sulfo fatty acid disalt (A) of general formula (I)

$$R^1CH(SO_3M^1)COOM^2 \qquad (I),$$

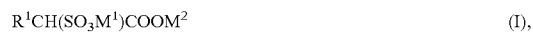

in which the radical $R^1$ is a linear or branched alkyl or alkenyl radical having 6 to 18 carbon atoms and the radicals $M^1$ and $M^2$, independently of each other, are selected from H, Li, Na, K, Ca/2, Mg/2, ammonium, and alkanolamine,
one or more sulfoketone (B) selected from compounds (F) and compounds (G)
wherein the compounds (F) have general formula (VI)

$$R^6CH_2—CO—CHR^7(SO_3M^8) \qquad (VI),$$

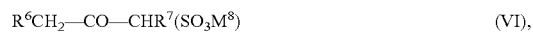

in which the radicals $R^6$ and $R^7$, independently of each other, are a linear or branched alkyl radical having 6 to 18 carbon atoms and the radical $M^8$ is selected from H, Li, Na, K, Ca/2, Mg/2, ammonium, and alkanolamine, and the compounds (G) have general formula (VII)

$$(SO_3M^9)R^8CH—CO—CHR^9(SO_3M^{10}) \qquad (VII),$$

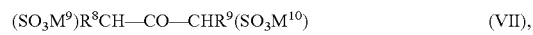

in which the radicals $R^8$ and $R^9$, independently of each other, are a linear or branched alkyl radical having 6 to 18 carbon atoms and the radicals $M^9$ and $M^{10}$, independently of each other, are selected from H, Li, Na, K, Ca/2, Mg/2, ammonium and, alkanolamine, and water,
wherein the amount of the compound (A) is greater than the amount of the compound (B), both based on the total aqueous surfactant composition. The compositions have good foaming ability, good skin compatibility, a pleasant sensory feel to the foam, and are suitable for cosmetic products, detergent, and cleaners.

7 Claims, No Drawings

(51) Int. Cl.

| | |
|---|---|
| *A61K 8/44* | (2006.01) |
| *A61K 8/46* | (2006.01) |
| *A61K 8/60* | (2006.01) |
| *A61Q 5/02* | (2006.01) |
| *A61Q 9/02* | (2006.01) |
| *A61Q 11/00* | (2006.01) |
| *A61Q 19/10* | (2006.01) |
| *C11D 1/37* | (2006.01) |
| *C11D 3/04* | (2006.01) |
| *C11D 10/04* | (2006.01) |
| *C11D 3/00* | (2006.01) |
| *C11D 1/04* | (2006.01) |
| *C11D 1/28* | (2006.01) |
| *C11D 1/66* | (2006.01) |
| *C11D 1/90* | (2006.01) |
| *C11D 1/12* | (2006.01) |

(56) References Cited

U.S. PATENT DOCUMENTS

| | | | |
|---|---|---|---|
| 2005/0153853 A1* | 7/2005 | Sajic | C11D 17/006 510/141 |
| 2009/0227482 A1* | 9/2009 | Dong | A61Q 5/02 510/125 |
| 2014/0076344 A1* | 3/2014 | Doi | A61Q 19/10 132/202 |
| 2017/0007520 A1 | 1/2017 | Brunn et al. | |
| 2017/0007523 A1 | 1/2017 | Max et al. | |
| 2017/0283741 A1 | 10/2017 | Behler et al. | |
| 2018/0119002 A1* | 5/2018 | Back | E21B 43/16 |

FOREIGN PATENT DOCUMENTS

| | | |
|---|---|---|
| EP | 2 902 011 A1 | 8/2015 |
| EP | 2 990 026 A1 | 3/2016 |
| WO | WO-98/44907 A1 | 10/1998 |

* cited by examiner

AQUEOUS SURFACTANT COMPOSITIONS

CROSS-REFERENCE TO RELATED APPLICATIONS

This is the U.S. national phase of International Application No. PCT/EP2017/061266, filed May 11, 2017, which claims the benefit of European Patent Application No. 16170189.1, filed May 18, 2016.

FIELD OF THE INVENTION

The present invention relates to aqueous surfactant compositions with a content of alpha-sulfo fatty acid disalts and specific sulfoketones.

PRIOR ART

Anionic surfactants are some of the most widespread interface-active compounds and, apart from being used in detergents and cleaners, are also used for diverse purposes in the field of cosmetics. Customary anionic surfactants as are used in particular in cosmetics are the salts of alkyl ether sulfates (alkyl polyether sulfates, fatty alcohol polyglycol ether sulfates, in short also ether sulfates). They are characterized by a strong foaming ability, high cleaning power, low sensitivity to hardness and grease and are used widely for producing cosmetic products such as, for example, hair shampoos, foam or shower baths, but also in hand dishwashing detergents.

For many current applications, apart from a good interface-active effect, further requirements are placed on anionic surfactants. A high dermatological compatibility is required in particular in cosmetics. In addition, good foaming ability and a pleasant sensory feel to the foam is generally desired. Furthermore, there is a need for anionic surfactants which can be produced at least partially from biogenic sources and specifically also renewable raw materials.

DESCRIPTION OF THE INVENTION

The object of the present invention was to provide aqueous surfactant compositions which are characterized by the properties specified below:
good foaming ability.
pleasant sensory feel to the foam.
good skin compatibility.

The invention firstly provides aqueous surfactant compositions comprising
one or more alpha-sulfo fatty acid disalts (A) of general formula (I),

in which the radical $R^1$ is a linear or branched alkyl or alkenyl radical having 6 to 18 carbon atoms and the radicals $M^1$ and $M^2$—independently of each other—are selected from the group comprising H, Li, Na, K, Ca/2, Mg/2, ammonium and alkanolamines, one or more sulfoketones (B) selected from the compounds (F) and the compounds (G), wherein the compounds (F) have general formula (VI)

in which the radicals $R^6$ and $R^7$—independently of each other—are a linear or branched alkyl radical having 6 to 18 carbon atoms and the radical $M^8$ is selected from the group comprising H, Li, Na, K, Ca/2, Mg/2, ammonium and alkanolamines, and wherein the compounds (G) have general formula (VII)

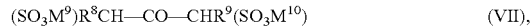

in which the radicals $R^8$ and $R^9$—independently of each other—are a linear or branched alkyl radical having 6 to 18 carbon atoms and the radicals $M^9$ and $M^{10}$—independently of each other—are selected from the group comprising H, Li, Na, K, Ca/2, Mg/2, ammonium and alkanolamines, and water,
where the following provisos apply:
the amount of the compounds (A) is greater than the amount of the compounds (B)—both based on the total aqueous surfactant composition.
if the aqueous surfactant composition one or more ester sulfonates (E) of general formula (V),

in which the radical $R^2$ is a linear or branched alkyl or alkenyl radical having 6 to 18 carbon atoms and the radical $R^3$ is a linear or branched alkyl or alkenyl radical having 1 to 20 carbon atoms, where the radical $R^3$ can logically be an alkenyl radical or be branched only above 3 carbon atoms, and the radical $M^7$ is selected from the group comprising Li, Na, K, Ca/2, Mg/2, ammonium and alkanolamines, it is the case that the compounds (A)—based on the totality of the compounds (A) and (E)—must be present to an extent of 50% by weight or more—and in particular to an extent of 90% by weight or more.

The aqueous surfactant compositions according to the invention are characterized by the following advantageous properties:

Good foaming ability and pleasant sensory feel to the foam. In this regard, it may be noted that particularly in the field of cosmetics, foaming ability can be understood to mean different aspects, for example it being possible to use any of foam volume, foam stability, foam elasticity, water content of the foam as well as optical features of the foam such as, for example, the pore size, for the purposes of assessing the foam. The compositions according to the invention have a large foam volume during the foaming. In practice, the initial foaming takes place within a relatively short period (from a few seconds to one minute). Typically, during initial foaming, a shower gel or a shampoo is spread and caused to foam by rubbing between hands, skin and/or hair. In the laboratory, the foaming behavior of an aqueous surfactant solution can be assessed e.g. by agitating the solution within a comparatively short time period by means of stirring, shaking, pumping, bubbling through a gas stream or in other way. Subjective assessment of the foam sensory feel can be made by test subjects. For this purpose, aspects such as creaminess, elasticity, moldability of the foam may be assessed.

Good skin and mucosa compatibility. These can be detected by in vitro methods known to those skilled in the art (e.g. RBC or HET-CAM) and also by test subjects (e.g. patch test).

Outstanding care performance on skin and hair. This can be assessed, for example in test subjects by reference to subjective skin feel (smoothness, dryness etc.) or haptics and feel of the treated hair. Mechanical measurement methods, such as combability of the hair, can also be used.

Good storage stability. This is then the case if the aqueous compositions do not exhibit any visible (e.g. cloudiness, discoloration, phase separation) or measurable (e.g. pH, viscosity, active substance content) changes.

Good applicability and processability. The compositions can be dissolved rapidly and without supply of heat on introducing in water.

Good clear solubility and transparency. The aqueous surfactant compositions do not have a tendency to precipitation or cloudiness.

Sufficiently high viscosity, which is understood in the context of the present invention to mean a value of 1000 mPas or higher (measured with a Brookfield RV laboratory rheometer at 23° C., 12 rpm, spindle set RV 02 to 07 (spindle choice depending on viscosity range)). As is known, "mPas" means millipascal seconds.

Good cleaning performance. The aqueous surfactant compositions are suitable for removing and emulsifying soiling, especially fat or oil-containing soiling, from solid or textile surfaces.

The Compounds (A)

The compounds (A), which are referred to within the context of the present invention as alpha-sulfo fatty acid disalts, are obligatory for the aqueous surfactant compositions according to the invention. They have the formula (I) specified above

$$R^1CH(SO_3M^1)COOM^2 \quad (I),$$

in which the radical $R^1$ is a linear or branched alkyl or alkenyl radical having 6 to 18 carbon atoms and the radicals $M^1$ and $M^2$—independently of each other—are selected from the group comprising H, Li, Na, K, Ca/2, Mg/2, ammonium and alkanolamines. In this connection, particularly preferred alkanolamines are monoethanolamine, diethanolamine, triethanolamine and monoisopropanolamine.

In one embodiment, the proviso applies that the proportion of the compounds (A) in the aqueous surfactant compositions in which the radical $R^1$ is an alkenyl radical—based on the total amount of the compounds (A)—is 3% by weight or less.

In a preferred embodiment, the radical $R^1$ in the formula (I) is a saturated, linear alkyl radical having 10 to 16 carbon atoms, where, with regard to the compounds (A) it is the case that the proportion of the compounds (A) in which the radical $R^1$ is a decyl and/or a dodecyl radical—based on the total amount of the compounds (A)—is 70% by weight or more and preferably 90% by weight or more.

In one embodiment, the radicals $M^1$ and $M^2$ in formula (I) are selected from the group comprising H (hydrogen) and Na (sodium).

The compounds (A) can be prepared by all methods known appropriately to the person skilled in the art. A particularly preferred method of preparation here is the sulfation of the corresponding carboxylic acids. Here, the corresponding carboxylic acid and in particular the corresponding fatty acids are reacted with gaseous sulfur trioxide, the sulfur trioxide being used preferably in an amount such that the molar ratio of $SO_3$ to fatty acid is in the range from 1.0:1 to 1.1:1. The crude products obtained in this way, which are acidic sulfation products, are then partially or completely neutralized, preference being given to complete neutralization with aqueous NaOH. If desired, it is also possible to undertake purification steps and/or a bleaching (for adjusting the desired pale color of the products).

In a particularly preferred embodiment, the compounds (A) are used in technical-grade form. This means that the corresponding carboxylic acids, in particular native fatty acid, are sulfated with gaseous sulfur trioxide, as a result of which, following partial or complete neutralization of the resulting acidic sulfation products, a mixture of the compounds (A), (C) and (D) results. By virtue of corresponding adjustments of the reaction parameters (in particular molar ratio of carboxylic acid and sulfur trioxide, and also reaction temperature) it is possible to control the ratio of the compounds (A), (C) and (D). The compounds (C) and (D) are described below in the chapter "Preferred embodiments".

In the context of the present invention, preference is given to those technical-grade mixtures of alpha-sulfo fatty acid disalts which have the following composition:
the content of (A) is in the range from 60 to 100% by weight,
the content of (C) is in the range from 0 to 20% by weight,
the content of (D) is in the range from 0 to 20% by weight,
with the proviso that the sum of the components (A), (C) and (D) in this mixture is 100% by weight.

The Compounds (B)

As detailed above, the aqueous surfactant compositions according to the invention, in addition to the compounds (A) and water, comprise one or more sulfoketones (B) selected from the compounds (F) and (G).

The compounds (F) have general formula (VI)

$$R^6CH_2—CO—CHR^7(SO_3M^8) \quad (VI),$$

in which the radicals $R^6$ and $R^7$—independently of each other—are a linear or branched alkyl radical having 6 to 18 carbon atoms and the radical $M^8$ is selected from the group comprising H, Li, Na, K, Ca/2, Mg/2, ammonium and alkanolamines. In this connection, particularly preferred alkanolamines are monoethanolamine, diethanolamine, triethanolamine and monoisopropanolamine.

In the context of the present invention, the compounds (F) are referred to as monosulfoketones.

In a preferred embodiment, the radicals $R^6$ and $R^7$ in the formula (VI)—independently of each other—are a saturated, linear radical having 10 to 16 carbon atoms, where, with regard to the compounds (F) it is the case that the proportion of the compounds (F) in which the radicals $R^6$ and $R^7$ are a decyl and/or a dodecyl radical—based on the total amount of the compounds (F)—is 70% by weight or more and preferably 90% by weight or more. In one embodiment, the radical $M^8$ in formula (VI) is selected from the group comprising H and Na.

The compounds (G) have general formula (VII)

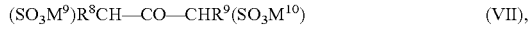
$$(SO_3M^9)R^8CH—CO—CHR^9(SO_3M^{10}) \quad (VII),$$

in which the radicals $R^8$ and $R^9$—independently of each other—are a linear or branched alkyl radical having 6 to 18 carbon atoms and the radicals $M^9$ and $M^{10}$—independently of each other—are selected from the group comprising H, Li, Na, K, Ca/2, Mg/2, ammonium and alkanolamines. In this connection, particularly preferred alkanolamines are monoethanolamine, diethanolamine, triethanolamine and monoisopropanolamine.

In the context of the present invention, the compounds (G) are referred to as disulfoketones.

In a preferred embodiment, the radicals $R^8$ and $R^9$ in the formula (VII)—independently of each other—are a saturated, linear radical having 10 to 16 carbon atoms, where, with regard to the compounds (G) it is the case that the proportion of the compounds (G) in which the radicals $R^8$ and $R^9$ are a decyl and/or a dodecyl radical—based on the total amount of the compounds (G)—is 70% by weight or more and preferably 90% by weight or more. In one embodiment, the radicals $M^9$ and $M^{10}$ in formula (VII) are selected from the group comprising H and Na.

The preparation of the compounds (F) and (G) is not subject to any particular restrictions and they can be prepared by all methods known to those skilled in the art.

In one embodiment, the compounds (F) and (G) are prepared by sulfonation of the corresponding ketones with gaseous sulfur trioxide, as described in the German published specification DE-A-42,20,580.

In other embodiment, the preparation of the compounds (F) and (G) starts from fatty acids. In this case, the sulfation of liquid fatty acids with gaseous sulfur trioxide is conducted such that, in addition to disalts (A), the compounds (F) and (G) are also formed, which can be accomplished as a result of carrying out the sulfation as follows: the ratio of fatty acid raw materials, which may also be used in the form of mixtures of fatty acids of different chain length, and sulfur trioxide is adjusted so that 1.0 to 1.5 mol and especially 1.0 to 1.25 mol of $SO_3$ are used per mole of fatty acid(s). The fatty acids are introduced into the reactor at a reservoir temperature in the range of 70 to 100° C. After the sulfation, the resulting liquid sulfation product is maintained and aged at this temperature for 5 to 20 minutes in a temperature-controlled post-reaction coil. Neutralization is then effected with an aqueous base, preferably sodium hydroxide, generally in a pH range of 5 to 10, especially 5 to 7. Subsequently, an acidic bleaching—the pH here is adjusted to a value of 7 or less—may be carried out with hydrogen peroxide.

Preferred Embodiments

In one embodiment, the aqueous surfactant compositions according to the invention comprise, besides the compounds (A), (B) and water, additionally one or more compounds (C) of general formula (III)

$$R^4COOM^5 \tag{III}$$

In the formula (III), the radical $R^4$ is a linear or branched alkyl or alkenyl radical with 7 to 19 carbon atoms and the radical $M^5$ is selected from the group comprising H, Li, Na, K, Ca/2, Mg/2, ammonium and alkanolamines. In this connection, particularly preferred alkanolamines are monoethanolamine, diethanolamine, triethanolamine and monoisopropanolamine.

In one embodiment, the aqueous surfactant compositions according to the invention comprise, besides the compounds (A), (B) and water, additionally one or more inorganic salts of sulfuric acid (D) of general formula (IV)

$$(M^6)_2SO_4 \tag{IV}$$

wherein $M^6$ is selected from the group comprising Li, Na, K, Ca/2, Mg/2, ammonium and alkanolamine. In this connection, particularly preferred alkanolamines are monoethanolamine, diethanolamine, triethanolamine and monoisopropanolamine.

In a preferred embodiment, the aqueous surfactant compositions according to the invention comprise the compounds (A), (B), (C), (D) and water. Particular preference is given to aqueous surfactant compositions comprising the compounds (A), (C), (D), (F) and (G). In this case, it is particularly preferable if the radicals $M^1$ and $M^2$ of the compounds (A), the radical $M^5$ of the compounds (C), the radical $M^6$ of the compounds (D), the radical $R^8$ of the compounds (F) and the radicals $M^9$ and $M^{10}$ of the compounds (G) are selected from the group comprising H and Na.

In one embodiment, the compositions according to the invention, in addition to the compounds (A), (B), (C), (D) and water, additionally comprise one or more compounds (H) selected from the group comprising alkyl glycosides (H1), amidoalkylbetaines (H2) and N-acylglutamic acid compounds (H3).

The compounds (H1), which in the context of the present invention are referred to as alkyl glycosides, have the formula (IIa), $$R^{10}O\text{-}[G]_p \tag{IIa}$$

in which $R^2$ is an alkyl and/or alkenyl radical having 8 to 18 carbon atoms, G is a sugar residue having 5 or 6 carbon atoms and p is a number between 1 and 10. With regard to the compounds (H1), the proviso also applies that the proportion of the compounds (H1) in which the radical $R^2$ is an alkyl or alkenyl radical having 15 or more carbon atoms—based on the total amount of the compounds (H1) in the aqueous surfactant compositions—is 5% by weight or less.

It may expressly be stated that the naming of the compounds (H1) as alkyl glycosides—henceforth also referred to as APGs (singular: APG)—serves merely for a linguistically simple naming of the compounds (H1) and should not be understood as being structurally limiting; hence in the definition according to the formula of the compounds (H1) it is clarified that the radical $R^{10}$ can mean either an alkyl or an alkenyl radical and also—as the index p shows—that they can be alkyl or alkenyl oligoglycosides.

APGs of the form claimed here can be obtained by the relevant methods of preparative organic chemistry. The APGs can be derived from aldoses or ketoses with 5 or 6 carbon atoms. Preferably, the APGs are derived from glucose.

The index number p in the general formula (IIa) specifies the degree of oligomerization (DP=degree of polymerization). The degree of oligomerization of the APGs is between 1 and 10 and preferably between 1 and 6. Whereas p in an individual APG molecule must always be an integer and here in particular assumes the values in the range from 1 to 6, the value p for an APG which is a mixture of different APG molecules, which differ in their individual p values, is an analytically determined calculated parameter which in most cases is a fraction. Preferably, APGs are used with an average degree of oligomerization p in the range from 1.1 to 3.0. In this connection, preference is given in particular to those APGs whose average degree of oligomerization is less than 2 and is preferably in the range from 1.1 to 1.8 and in particular in the range from 1.2 to 1.7.

The average degree of oligomerization here is to be understood in the sense of how it is defined in the monograph K. Hill, W. von Rybinski, G. Stoll "Alkyl Polyglycosides. Technology, Properties and Applications" (VCH-Verlagsgesellschaft, 1996) in the section "Degree of polymerization" (compare pages 11-12 of the book): Therein it reads "The average number of glycose units linked to an alcohol group is described as the (average) degree of polymerization (DP)." In explanatory FIG. 2, which describes a typical distribution of dodecyl glycoside oligomers of an AOPG with a DP of 1.3, the average DP is also described by a corresponding mathematical formula.

The radical $R^{10}$ is preferably derived from primary alcohols having 4 to 11 carbon atoms and preferably 8 to 10 carbon atoms. Typical examples of suitable radicals $R^{10}$ are butyl, hexyl, octyl, decyl, undecyl, dodecyl and myristyl. They are derived from the saturated fatty alcohols butanol-1, caproic alcohol (hexanol-1), caprylic alcohol (octanol-1), capric alcohol (decanol-1), undecanol-1, lauryl alcohol (dodecanol-1) and myristyl alcohol (tetradecanol-1), as are obtained for example in the hydrogenation of technical-grade fatty acid methyl esters or in the course of the hydrogenation of aldehydes during Roelen oxo synthesis.

Preference is given to APGs which are derived from glucose and in which the radical $R^{10}$ is a saturated alkyl radical having 8 to 12 carbon atoms and which have an average degree of oligomerization in the range from 1.1 to 3 and in particular in the range from 1.2 to 1.8 and particularly preferably in the range from 1.2 to 1.7. These APGs can for example be prepared by reacting a sugar, in particular glucose, under acid catalysis with a fatty alcohol mixture, the fatty acid mixture used preferably being a forerunning produced during the distillative separation of technical-grade $C_{8-18}$-coconut fatty alcohol, which comprises predominantly octanol-1 and decanol-1 and also small amounts of dodecanol-1.

The compounds (H2), which in the context of the present invention are referred to as amidoalkylbetaines, have the formula (IIb),

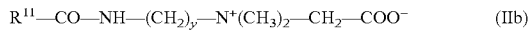

$$R^{11}-CO-NH-(CH_2)_y-N^+(CH_3)_2-CH_2-COO^- \quad \text{(IIb)}$$

in which the radical $R^{11}$ is a linear or branched alkyl or alkenyl radical having 7 to 19 carbon atoms and the index y is an integer in the range 2 to 4. Also applicable—as likewise stated above—is the proviso that the proportion of the compounds (H2) in which the radical $R^2$ is an alkenyl radical—based on the total amount of the compounds (H2) in the aqueous surfactant compositions—is 3% by weight or less.

The compounds (H2) can be prepared by all of the methods known appropriately to the person skilled in the art.

In one embodiment, the index y in the formula (IIb) is the number 3.

In one embodiment, $R^{11}$ in the formula (IIb) is a saturated, linear radical having 11 to 17 carbon atoms where, with regard to the compounds (H2), it is the case that the proportion of the compounds (H2) in which the radical $R^{11}$ is an undecyl or a tridecyl radical—based on the total amount of the compounds (H2)—is 60% by weight or more.

In a preferred composition, the compounds (H2) are cocamidopropylbetaine. It is an industrially available product which is typically produced in two steps:

Firstly, coconut fatty acid is reacted with dimethylaminopropylamine (DMAPA, chemical formula $NH_2-(CH_2)_3-N(CH_3)_2$). The resulting amide here is then reacted in a second step with sodium chloroacetate (chemical formula $Cl-CH_2-COONa$) in the presence of NaOH, a quaternization taking place with the elimination of NaCl. The product of technical grade thus obtainable can comprise, besides cocamidopropylbetaine and NaCl, as a consequence of production, as byproducts, glycerol, partial glycerides, glycolic acid, diglycolic acid and free fatty acid, it being possible to reduce the content of these byproducts through the choice of suitable production conditions. If desired, these byproducts can also be further reduced in their content or be eliminated entirely by means of additional purification steps.

The compounds (H3), which in the context of the present invention are referred to as N-acylglutamic acid compounds, have the formula (IIc),

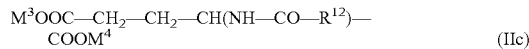

$$M^3OOC-CH_2-CH_2-CH(NH-CO-R^{12})-COOM^4 \quad \text{(IIc)}$$

in which the radical $R^{12}$ is a linear or branched alkyl or alkenyl radical having 7 to 19 carbon atoms and the radicals $M^3$ and $M^4$—independently of each other—are selected from the group comprising H, Li, Na, K, Ca/2, Mg/2, ammonium and alkanolamines. In this connection, particularly preferred alkanolamines are monoethanolamine, diethanolamine, triethanolamine and monoisopropanolamine. In one embodiment, the radicals $M^3$ and $M^4$ are selected from the group comprising H and Na.

If desired, the aqueous surfactant compositions according to the invention can additionally comprise one or more further surfactants which, in structural terms, do not belong to the aforementioned compounds (A), (B), (D), (E), (F) or (G). These surfactants may be anionic, cationic, nonionic or amphoteric surfactants.

Use of the Compositions

A further subject matter of the invention is the use of the aforementioned compositions for cosmetic products, and also detergents and cleaners.

With regard to cosmetic products, particular preference is given here especially to those which are present in the form of hair shampoos, shower gels, soaps, syndets, washing pastes, washing lotions, scrub preparations, foam baths, oil baths, shower baths, shaving foams, shaving lotions, shaving creams and dental care products (for example toothpastes, mouthwashes and the like).

With regard to cleaners, of preference here are in particular products with a low pH for cleaning hard surfaces, such as bath and toilet cleaners and the like, and also for cleaning and/or fragrance gels for use in sanitary installations.

The invention claimed is:

1. An aqueous surfactant composition comprising
one or more alpha-sulfo fatty acid disalt (A) of general formula (I)

$$R^1CH(SO_3M^1)COOM^2 \quad \text{(I)},$$

in which the radical $R^1$ is a saturated, linear alkyl radical having 10 to 16 carbon atoms and the radicals $M^1$ and $M^2$, independently of each other, are selected from the group consisting of H, Li, Na, K, Ca/2, Mg/2, ammonium, and alkanolamine, one or more sulfoketone (B) selected from compound (F) and compound (G), in which the compound (F) has a general formula (VI)

$$R^6CH_2-CO-CHR^7(SO_3M^8) \quad \text{(VI)},$$

in which the radicals $R^6$ and $R^7$, independently of each other, are a linear or branched alkyl radical having 6 to 18 carbon atoms and the radical $M^8$ is selected from the group consisting of H, Li, Na, K, Ca/2, Mg/2, ammonium, and alkanolamine, and wherein the compound (G) has a general formula (VII)

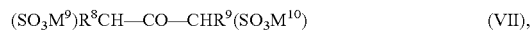

$$(SO_3M^9)R^8CH-CO-CHR^9(SO_3M^{10}) \quad \text{(VII)},$$

in which the radicals $R^8$ and $R^9$, independently of each other, are a linear or branched alkyl radical having 6 to 18 carbon atoms and the radicals $M^9$ and $M^{10}$, independently of each other, are selected from the group consisting of H, Li, Na, K, Ca/2, Mg/2, ammonium, and alkanolamine, one or more compound (C) of general formula (III)

$$R^4COOM^5 \quad \text{(III)},$$

in which the radical $R^4$ is a linear or branched alkyl or alkenyl radical having 7 to 19 carbon atoms and the radical $M^5$ is selected from the group consisting of H, Li, Na, K, Ca/2, Mg/2, ammonium, and alkanolamine, one or more inorganic salt of sulfuric acid (D) of general formula (IV)

$$(M^6)_2SO_4 \quad (IV),$$

wherein $M^6$ is selected from the group comprising Li, Na, K, Ca/2, Mg/2, ammonium, and alkanolamine, and water, where the following provisos apply:

an amount of the compound (A) is greater than an amount of the compounds (B), both based on the total aqueous surfactant composition;

the content of compound (A) is in the range from 60 to 100% by weight based on the sum of compounds (A), (C), and (D) in the aqueous surfactant composition;

the content of compound (C) is in the range from more than 0 to 20% by weight based on the sum of compounds (A), (C), and (D) in the aqueous surfactant composition;

the content of compound (D) is in the range from more than 0 to 20% by weight based on the sum of compounds (A), (C), and (D) in the aqueous surfactant composition;

if the aqueous surfactant composition contains one or more ester sulfonate (E) of general formula (V)

$$R^2CH(SO_3M^7)COOR^3 \quad (V),$$

in which the radical $R^2$ is a linear or branched alkyl or alkenyl radical having 6 to 18 carbon atoms and the radical $R^3$ is a linear or branched alkyl or alkenyl radical having 1 to 20 carbon atoms, where the radical $R^3$ can be an alkenyl radical or be branched only above 3 carbon atoms, and the radical $M^7$ is selected from the group consisting of Li, Na, K, Ca/2, Mg/2, ammonium, and alkanolamine, it is the case that the compounds (A), based on the totality of the compounds (A) and (E), must be present to an extent of 50% by weight or more; and with regard to the compound (A) it is the case that the proportion of the compound (A) in which the radical $R^1$ is a decyl or a dodecyl radical, based on the total amount of the compounds (A), is 90% by weight or more.

2. The composition according to claim 1, wherein the radicals $M^1$ and $M^2$ and also the radicals $M^8$, $M^9$, and $M^{19}$ are selected from H (hydrogen) and Na (sodium).

3. The composition according to claim 1, wherein the composition additionally comprises one or more compound (H) selected from the group consisting of alkyl glycosides (H1), amidoalkylbetaines (H2), and N-acylglutamic acid compounds (H3), wherein the compounds (H) are characterized as follows: the compound (H1) by the formula $R^{10}O\text{-}[G]_p$ (IIa), in which $R^2$ is an alkyl and/or alkenyl radical having 8 to 18 carbon atoms, G is a sugar residue having 5 or 6 carbon atoms and p is a number between 1 and 10, wherein with respect to the compounds (H1) the further proviso applies that the proportion of the compounds (H1), in which the radical $R^2$ is an alkyl or alkenyl radical having 15 carbon atoms or more, based on the total amount of the compounds (H1) in the aqueous surfactant compositions, is 5% by weight or less, the compound (H2) is characterized by the formula (IIb) $R^{11}\text{—CO—NH—}(CH_2)_y\text{—N}^+(CH_3)_2\text{—}CH_2\text{—COO}^-$ (IIb), in which the radical $R^{11}$ is a linear or branched alkyl or alkenyl radical having 7 to 19 carbon atoms and the index y is an integer in the range from 2 to 4, wherein the proviso applies that the proportion of the compounds (H2), in which the radical $R^2$ is an alkenyl radical, based on the total amount of the compounds (H2) in the aqueous surfactant compositions, is 3% by weight or less and the compounds (H3) by the formula $M^3OOC\text{—}CH_2\text{—}CH_2\text{—}CH(NH\text{—}CO\text{—}R^{12})\text{—}COOM^4$ (IIc), in which the radical $R^{12}$ is a linear or branched alkyl or alkenyl radical having 7 to 19 carbon atoms and the radicals $M^3$ and $M^4$, independently of each other, are selected from the group consisting of H, Li, Na, K, Ca/2, Mg/2, ammonium and alkanolamines.

4. The composition according to claim 1, wherein the composition additionally comprises one or more amidoalkylbetaine (H2), wherein the compound (H2) is characterized by a formula (IIb) $R^{11}\text{—CO—NH—}(CH_2)_y\text{—N}^+(CH_3)_2\text{—}CH_2\text{—COO}^-$ (IIb), in which the radical $R^{11}$ is a linear or branched alkyl or alkenyl radical having 7 to 19 carbon atoms and the index y is an integer in the range from 2 to 4, wherein the proviso applies that the proportion of the compounds (H2), in which the radical $R^2$ is an alkenyl radical, based on the total amount of the compounds (H2) in the aqueous surfactant compositions, is 3% by weight or less.

5. The composition according to claim 1 for use in cosmetic products, detergents, and cleaners.

6. The composition according to claim 1 for use in cosmetic products in the form of hair shampoos, shower gels, soaps, syndets, washing pastes, washing lotions, scrub preparations, foam baths, oil baths, shower baths, shaving foams, shaving lotions, shaving creams, and dental care products.

7. The composition according to claim 1 for use in products with a low pH for cleaning hard surfaces.

* * * * *